(12) United States Patent
Fang et al.

(10) Patent No.: US 11,926,709 B2
(45) Date of Patent: *Mar. 12, 2024

(54) METHOD FOR RECYCLING WASTE POLYESTER

(71) Applicant: AVANTGARDE (SHANGHAI) ENVIRONMENTAL TECHNOLOGY CO., LTD., Shanghai (CN)

(72) Inventors: Huayu Fang, Shanghai (CN); Enbin Zhu, Shanghai (CN); Dubin Wang, Shanghai (CN); Guoqing Yu, Shanghai (CN); Jincheng Chen, Shanghai (CN); Tianyuan Li, Shanghai (CN); Jiantong Wu, Shanghai (CN); Jianhua Chen, Shanghai (CN); Shengyao Lin, Shanghai (CN)

( * ) Notice: Subject to any disclaimer, the term of this patent is extended or adjusted under 35 U.S.C. 154(b) by 260 days.

This patent is subject to a terminal disclaimer.

(21) Appl. No.: 17/013,674

(22) Filed: Sep. 7, 2020

(65) Prior Publication Data

US 2021/0024718 A1 Jan. 28, 2021

Related U.S. Application Data

(63) Continuation-in-part of application No. PCT/CN2020/076452, filed on Feb. 24, 2020.

(30) Foreign Application Priority Data

Jul. 10, 2019 (CN) .......................... 201910617915.X

(51) Int. Cl.
C08J 11/22 (2006.01)
C07C 67/02 (2006.01)
C07C 69/82 (2006.01)

(52) U.S. Cl.
CPC .............. C08J 11/22 (2013.01); C07C 67/02 (2013.01); *C07C 69/82* (2013.01); *C08J 2367/02* (2013.01)

(58) Field of Classification Search
CPC ........ C08J 11/02; C08J 11/24; C08J 2367/00; C08J 11/16
USPC ....... 521/48.5; 528/190, 192, 193, 194, 271, 528/272, 274
See application file for complete search history.

(56) References Cited

U.S. PATENT DOCUMENTS

| | | | | |
|---|---|---|---|---|
| 6,472,557 B1 * | 10/2002 | Pell, Jr. | .................. | C07C 67/03 560/96 |
| 2021/0024717 A1 * | 1/2021 | Fang | ....................... | C08J 11/24 |
| 2021/0040287 A1 * | 2/2021 | Fang | ....................... | C08J 11/24 |

* cited by examiner

*Primary Examiner* — Terressa Boykin

(57) ABSTRACT

A method for recycling waste polyester, in particular to a method for recycling waste polyester by a modified alcoholysis method to recycle waste polyester to prepare dimethyl terephthalate (DMT), is provided and belongs to waste polyester recycling technology field. The waste polyester after dewatering and deoxygenation treatment is used as a raw material, in the step of feeding in melted state the alcoholysis agent is added in the melted waste polyester for preliminary alcoholysis, and the alcoholysis agent is ethylene glycol. On one hand, alcoholysis reaction occurs when the waste polyester raw material are melted, and at the same time, the viscosity of the melted material is reduced. Thus, the melted material remains melted at the alcoholysis temperature and is not easy to solidify again after entering the alcoholysis tank, ensuring that the alcoholysis is carried out under homogeneous conditions.

11 Claims, 1 Drawing Sheet

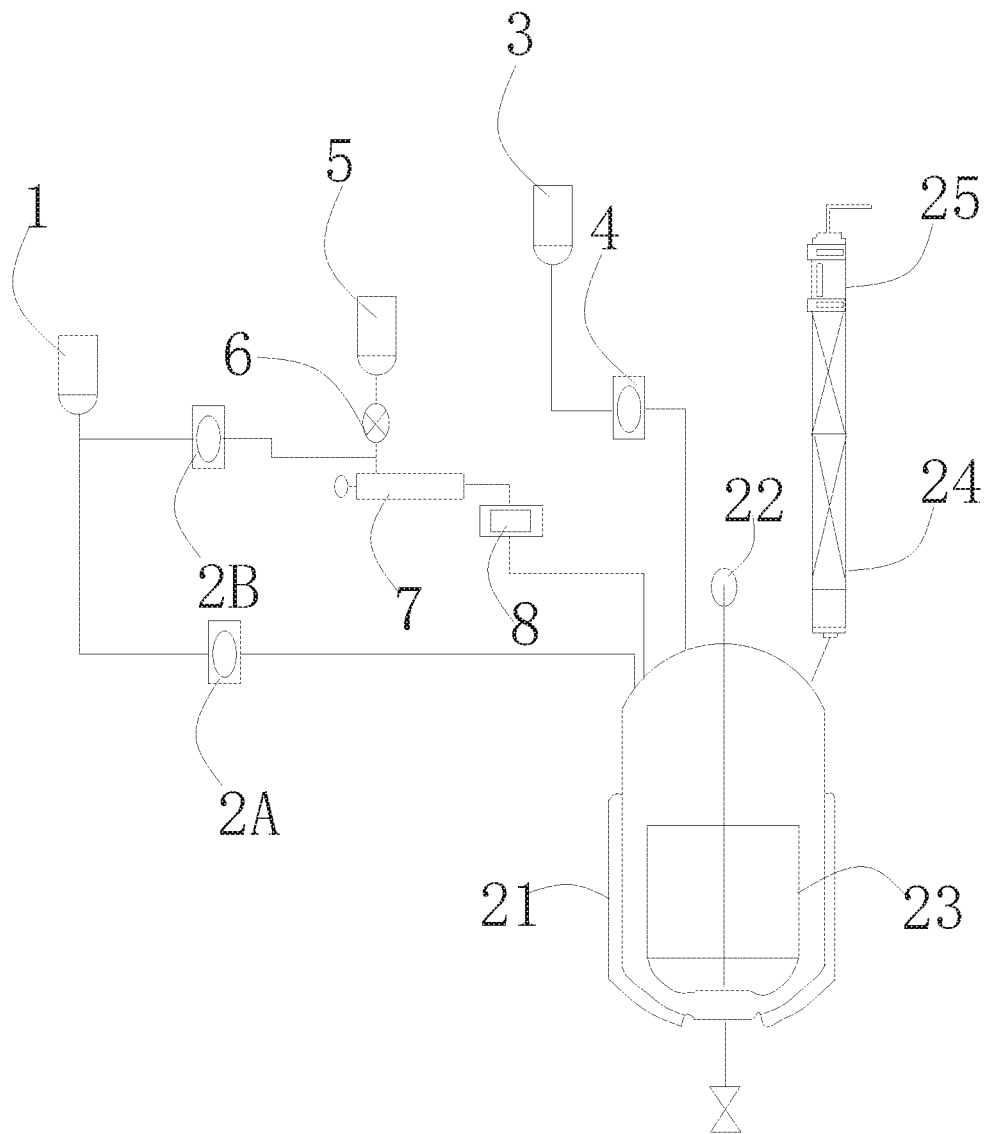

METHOD FOR RECYCLING WASTE POLYESTER

BACKGROUND OF THE INVENTION

1. Field of the Invention

The present invention belongs to waste polyester recycling technology field and relates to a method for recycling waste polyester, in particular to a method for recycling waste polyester by a modified alcoholysis method to recycle waste polyester to prepare dimethyl terephthalate (DMT).

2. Description of the Prior Art

Polyester (polyethylene terephthalate, PET) is the most produced synthetic fiber material, widely used in fiber, textile fabrics, clothing, polyester bottles, films, sheets and other products. Based on the needs of enhanced environmental awareness, resource conservation and sustainability, how to deal with the scraps produced in the manufacture of polyester products and the waste generated from the use of polyester products has become an urgent problem to be solved, and the recycling of waste polyester has become a development direction of green textile.

At present, the recycling methods of waste polyester mainly include physical recycling and chemical recycling methods. The physical recycling methods are relatively simple and economic, but the performance of the recycled product is poor. The chemical recycling methods mainly include hydrolysis method, alcoholysis method, ammonolysis method, amine hydrolysis method, thermal cracking method and other degradation methods. An important direction of the chemical recycling method is the alcoholysis of waste polyester with ethylene glycol (EG) into bishydroxy terephthalate (BHET) or oligomers, and then through transesterification in methanol to produce Dimethyl Terephthalate (DMT) and ethylene glycol. Pure DMT is obtained through purification and used as a raw material for polyester production, while methanol and ethylene glycol are used in the reaction system through purification and recycling to achieve the recycling of waste polyester.

The U.S. Pat. No. 6,706,843B1 provides a method for recycling waste polyester to produce DMT. The patent uses EG with a weight of 0.5-20 times the weight of the waste polyester and alcoholizes the waste polyester in the presence of a catalyst and at a temperature of 175° C.-190° C. Then, the alcoholysis product is distilled and concentrated to distill out EG, and the weight ratio of EG to waste polyester in the concentrated alcoholysis product is controlled in 0.5-2. The concentrated alcoholysis product is then transesterified with methanol to form DMT and purified by rectification to produce pure DMT. This technology adopts solid polyester and EG alcoholysis reaction. The alcoholysis reaction is a solid-liquid heterogeneous reaction with long reaction time. At the same time, in the alcoholysis process of waste polyester, the amount of EG used for alcoholysis is large. In order to carry out the transesterification reaction well, it is necessary to distill out part of the EG in the alcoholysis product, which has a process of concentrating the alcoholysis product, leading to an increase in input equipment and energy consumption.

SUMMARY OF THE INVENTION

Therefore, it is necessary to provide a method for recycling waste polyester to solve the problems of long depolymerization time and large dosage of alcoholysis agent caused by the solid-liquid heterogeneous reaction during alcoholysis in the prior art.

In order to achieve the above objective, a method for recycling waste polyester is provided and includes the following steps:

material pretreatment: dewatering and deoxidizing waste polyester material to obtain waste polyester as raw material;

feeding in melted state: melting waste polyester to obtain melted waste polyester and feeding the melted waste polyester to the alcoholysis tank, wherein the alcoholysis agent is added in the melted waste polyester for preliminary alcoholysis and the alcoholysis agent is ethylene glycol;

alcoholysis: the melted waste polyester, alcoholysis agent, and alcoholysis catalyst undergo depolymerization reaction in the alcoholysis tank to obtain alcoholysis product; and transesterification: the transesterification agent, a transesterification catalyst and the alcoholysis product undergo transesterification reaction in the transesterification tank.

Compared with the prior art, the present invention includes at least the following beneficial effects:

The waste polyester recycling method of the present invention uses the waste polyester after dewatering and deoxygenation treatment as a raw material, In the step of feeding in melted state, the alcoholysis agent is added in the melted waste polyester for preliminary alcoholysis, and the alcoholysis agent is ethylene glycol. On one hand, it can accelerate the melting of waste polyester in melting equipment. On the other hand, alcoholysis reaction occurs after the waste polyester is melted, and at the same time, the viscosity of the melted material is reduced. The melted material remains melted at the alcoholysis temperature and is not easy to solidify again after entering the alcoholysis tank, ensuring that the alcoholysis is carried out under homogeneous conditions.

BRIEF DESCRIPTION OF THE DRAWINGS

The drawing is a schematic diagram of the alcoholysis process flow in the recycling method of waste polyester according to the specific embodiment of the present invention.

DESCRIPTION OF THE PREFERRED EMBODIMENTS

In order to explain the technical content, structural features, achieved objectives, and effects of the technical solution in detail, the following describes it in detail with reference to specific embodiments and accompanying drawings.

The method for recycling waste polyester provided by the present disclosure includes the following steps:

Material pretreatment: dewatering and deoxidizing waste polyester material to obtain waste polyester raw material; feeding in melted state: melting waste polyester raw material to obtain melted waste polyester, which is continuously fed to the alcoholysis tank; alcoholysis: the melted waste polyester, alcoholysis agent, and alcoholysis catalyst undergo depolymerization reaction in the alcoholysis tank to obtain alcoholysis product; transesterification: the transesterification reaction occurs between the transesterification agent, the transesterification catalyst and the alcoholysis product in the transesterification tank; in the step of feeding in melted state, the alcoholysis agent is added in the melted waste polyester for preliminary alcoholysis, and the alcoholysis agent is ethylene glycol.

Through extensive research, the inventor has discovered that the length of depolymerization time and its depolymerization effect are the key to the recycling of waste polyester. When the alcoholysis method is used to depolymerize waste polyester, alcoholysis under homogeneous and liquid-liquid state greatly shortens the polymerization reaction time than alcoholysis under heterogeneous and solid-liquid state, and the purity and yield of the depolymerized product, i.e. Bis (2-hydroxyethyl) terephthalate (BHET), are also improved. Before entering the alcoholysis tank, the waste polyester can be fully melted into a liquid phase. When it is fed into the melting equipment such as a screw extruder, the alcoholysis agent, i.e. ethylene glycol, is added in proportion to make it partially alcoholic, thus promoting melting and reducing viscosity. Therefore, after the melted material enters the alcoholysis tank, it remains melted at the alcoholysis temperature and is not easy to solidify again, ensuring that the alcoholysis is carried out under homogeneous conditions.

The melted waste polyester, alcoholysis agent, and alcoholysis catalyst are fed into the alcoholysis tank under homogeneous and liquid-liquid state for alcoholysis reaction. The preferred solution is feeding continuously in melted state. The waste polyester added with ethylene glycol is alcoholized preliminarily and melted through a screw extruder. The conveying amount of the melted waste polyester is adjusted by the rotation speed of the screw extruder. The alcoholysis agent and the alcoholysis catalyst are also continuously fed into the alcoholysis tank in a liquid state with a predetermined amount controlled by a metering pump, and the alcoholysis product is obtained through the alcoholysis reaction. The rotation speed of the metering pumps 2A and 2B and the rotation speed of the waste polyester screw 9 are adjusted by a fixed ratio.

Due to the existence of the material in the alcoholysis tank, the waste polyester which is fed into the alcoholysis tank in a melted state and stirred by stirrer 23 is mixed with the original material, new EG, and new catalysts uniformly, and undergoes homogeneous alcoholysis in the melted state.

Furthermore, the alcoholysis product, the transesterification agent and the transesterification catalyst are sent together into the transesterification tank for the transesterification reaction. This step can also be fed in batch or continuous mode. However, compared with discontinuous reaction in batch mode, the yield and purity of DMT obtained by continuous feeding for transesterification step can be greatly improved.

Furthermore, after the waste polyester is dried/dewatered and deoxidized by the conventional processes and the melted polyester is processed by the screw extruder. The possibility of side reactions is greatly reduced, ensuring the purity and reaction efficiency of alcoholysis product and transesterification product in the subsequent processes.

Furthermore, the state of waste polyester has a greater impact on the process of heating and impelling the feed in the screw extruder. Thus, the waste polyester to be depolymerized is processed into 5 mm-10 mm×5 mm-10 mm uniform pellets by a densification process. The densification process can adopt conventional techniques, such as densification by rubbing, densification by melting, etc., to pretreat waste polyester. It is easy to understand that one or more of waste polyester bottle flakes, polyester film, polyester fiber, and waste textiles can be processed into uniform pellets as raw material through densification process, or the waste polyester can also be directly purchased and processed into uniform pellets as raw material.

In the present disclosure, the densification by rubbing is a process in which the special rubbing machine is used and the processing temperature is about 180 degrees. In the process of the densification by rubbing, the waste polyester is not completely melted and made into uniform particles. The densification by melting refers to pelletizing by a slicer after melting, the size of the slice is 3×4 mm, and the process temperature must reach about 280 degrees.

The inventors further discovered that when the waste polyester is melted in the preliminary alcolysis, the dosage of alcoholysis agent, i.e. ethylene glycol, has a great influence on the degree of preliminary alcoholysis. The dosage of alcoholysis agent, ethylene glycol, should make the polyester undergo preliminary alcoholysis and reduce the viscosity of the melt to facilitate the filtration before entering the alcoholysis tank. At the same time, due to the decrease in viscosity of the melt, the power of the screw extruder can be decreased. And the melting point of the polyester is decreased after the preliminary alcoholysis with the ethylene glycol. After entering the alcoholysis tank, it remains melted at the preset temperature in the alcoholysis tank, and it is not easy to solidify again, which is beneficial to alcoholysis.

In some embodiment, in the preliminary alcoholysis, based on the weight of the waste polyester raw material, the weight percentage of the dosage of the alcoholysis agent is 10 ppm-5%.

Furthermore, the melted waste polyester, alcoholysis agent, and alcoholysis catalyst are first fed to the first alcoholysis tank to perform the first alcoholysis reaction to obtain the first alcoholysis product, and the first alcoholysis product is then fed to the second alcoholysis tank which is connected in series with the first alcoholysis tank to perform the second alcoholysis reaction to obtain the alcoholysis product. And so on, multiple alcoholysis tanks can be connected in series to carry out the alcoholysis reaction more thoroughly and efficiently by such multiple continuous alcoholysis reactions. The content of BHET monomer in the obtained alcoholysis product can be as high as 75%, so that the yield and purity of DMT obtained in the transesterification step are higher.

In some embodiment, the alcoholysis tank includes a first alcoholysis tank and a second alcoholysis tank connected in series.

Furthermore, the weight ratio of the alcoholysis agent compared to the waste polyester raw material has a certain influence on the depolymerization reaction. If the amount of alcoholysis agent is too high, other by-products will be generated in the alcoholysis product because the excessive alcoholysis agent is mixed. If the amount of alcoholysis agent is too low, the alcoholysis will be incomplete and there will be more long-chain waste polyester in the alcoholysis product. Both of these conditions will affect the quality stability of the alcoholysis product, thereby affecting the subsequent transesterification reaction.

In some embodiment, in the alcoholysis step, the weight ratio of the melted waste polyester, alcoholysis agent, and alcoholysis catalyst is 1:1.0-2.0:0.003-0.03.

In some embodiment, the alcoholysis catalyst is potassium carbonate or zinc acetate and is prepared into an ethylene glycol solution with a mass concentration of 10%-70% and added into the alcoholysis tank.

In some embodiment, the transesterification agent commonly used in this field is selected as the transesterification agent of the present disclosure, but its dosage has a certain influence on the subsequent transesterification reaction. If it is added too little, the reaction will not be complete. And if it is added too much, the energy consumption will be increased.

In some embodiment, the transesterification agent is methanol, and the weight ratio of the melted waste polyester to the transesterification agent is 1:1 to 3.0.

Furthermore, the type and dosage of the transesterification catalyst have a certain influence on the speed of the transesterification reaction and the quality of the product. Increasing the amount of catalyst within a certain range cannot achieve the purpose of continuing to accelerate the rate of the transesterification reaction. On the contrary, excessive catalyst may lead to initiate other side reactions, produce other unnecessary by-products, and reduce the quality of the product. A small dosage of catalyst results in slow reaction speed and low reaction efficiency.

In some embodiment, the transesterification catalyst is sodium hydroxide or potassium carbonate, and the weight ratio of the melted waste polyester to the transesterification catalyst is 1:0.002-0.05.

In some embodiment, the weight ratio of the melted waste polyester to the transesterification catalyst is 1:0.003-0.02.

In some embodiment, the transesterification catalyst is prepared into an ethylene glycol solution with a mass concentration of 10%-70% and added to the transesterification tank.

Furthermore, the reaction temperature and reaction time in the alcoholysis kettle play a certain role in the quality stability of the product. The too low alcoholysis temperature is not beneficial to the progress of the alcoholysis reaction, and the too high alcoholysis temperature will cause the occurrence of side reactions. The process conditions of the transesterification reaction in the transesterification tank also have a certain impact on the final transesterification reaction product. The composition, activity and interaction of the material in the transesterification reactor should be fully considered in the determination of reaction temperature and reaction time.

In some embodiment, the reaction temperature is 180° C.-200° C. and the reaction time is 60 min-120 min in the alcoholysis step. In the transesterification step, the reaction temperature is 60° C.-80° C. and the reaction time is 30 min-90 min.

The raw DMT obtained by the transesterification reaction is continuously fed to the intermediate material storage tank and is used for the crystallization, separation and purification of the raw DMT in the next step. The crystallization, separation and purification of the raw DMT are carried out by conventional processes.

In order to describe in detail the technical content, structural features, achieved objectives and effects of the instant application, the following detailed descriptions are given in conjunction with the drawings and specific embodiments. It should be understood that these embodiments are only used to illustrate the application and not to limit the scope of the instant application.

Embodiment 1

The raw material is granulated as waste polyester pellets. After testing, the intrinsic viscosity of the polyester pellet is 0.62 dl/g, the melting point is 260° C., the average particle size is <10 mm, and the moisture content is <0.5%. The waste polyester pellets are fed into the screw extruder 7 from the waste polyester tank 5 through the rotary feeder 6 and melted therein, and then filtered through the filter 8 to remove un-melted impurities. Thereafter the melted material is continuously sent to the alcoholysis tank 21. The melting temperature of the screw extruder 7 is 275° C., and the filtration accuracy, i.e. pore size, of the filter 8 is 150 μm.

In the process of melting the above-mentioned waste polyester pellets in the screw extruder 7, ethylene glycol (EG) of 1 wt % of the waste polyester mass is added. Ethylene glycol is added quantitatively from the ethylene glycol storage tank 1 through the second metering pump 2B. By adjusting the ratio of the rotation speed of the second metering pump 2B to the rotation speed of the screw extruder 7, the ratio of the dosage of ethylene glycol to that of waste polyester pellets is adjusted. After ethylene glycol is added, the viscosity of the melt was 0.40 dl/g, the melting point was 232° C., and the switching cycle of the filter 8 is 20 days.

The melted waste polyester is continuously fed into the first alcoholysis tank 21 at a speed of 1000 kg/hr, and the conveying amount of the material is adjusted by the rotation speed of the screw extruder 7. The rotation speed is controlled based on the liquid level of the first alcoholysis tank 21 to achieve a relatively stable liquid level of the first alcoholysis tank 21.

The ethylene glycol in the ethylene glycol storage tank 1 and the alcoholysis catalyst in the alcoholysis catalyst storage tank 3 are transported into the alcoholysis tank 21 through the first metering pump 2A and the alcoholysis catalyst metering pump 4, respectively. The rotation speeds of the first metering pump 2A and the alcoholysis catalyst metering pump 4 and the rotation speed of the screw extruder 7 are adjusted to a fixed ratio. The feed rate of ethylene glycol is 1500 kg/h. The alcoholysis catalyst is an ethylene glycol solution containing potassium carbonate, the mass concentration of potassium carbonate in the ethylene glycol solution is 25%, and the feed rate of the alcoholysis catalyst is 80 kg/h.

In the alcoholysis tank 21, 2000 kg of alcoholysis material of the same composition is placed in advance. After the melted waste polyester is fed into the alcoholysis tank 21 and is stirred by the stirrer 23 therein. The original material in the alcoholysis tank 21, the newly fed alcoholysis agent ethylene glycol, and the newly fed alcoholysis catalyst potassium carbonate solution are mixed uniformly and undergo homogeneous alcoholysis in the melted state. The alcoholysis temperature is 190° C., and the material residence time, alcoholysis time, is 60 min. The content of monomers in alcoholysis product is 80% and the total content of monomers, dimers, trimers and tetramers is 98%.

The alcoholysis product obtained from the alcoholysis process in the alcoholysis tank 21 is added to the transesterification tank in a preset amount, and the transesterification agent (i.e. methanol), the transesterification catalyst and the alcoholysis product are put into the transesterification tank in a fixed ratio. The alcoholysis product and methanol undergo transesterification in the presence of a transesterification catalyst to produce raw DMT. In the present disclosure, the weight ratio of the alcoholysis product to methanol is indirectly represented as the original waste polyester to methanol, and the original waste polyester to methanol is 1:2. The transesterification catalyst is potassium carbonate, and the amount of potassium carbonate is 2.0 wt % of the waste polyester. Potassium carbonate is added in the form of ethylene glycol solution, and the concentration of potassium carbonate in the ethylene glycol solution is 25%. The reaction temperature is 75° C., the reaction time is 70 min, and the transesterification product is obtained in the transesterification reaction.

The above-mentioned transesterification product enters the DMT crystallizer from the intermediate material storage tank, and the temperature of the material is cooled to below 40° C., and DMT crystallizes and precipitates. After filtration, a raw DMT filter cake and filtrate are obtained. The raw DMT filter cake is washed with methanol several times to obtain a DMT filter cake. The DMT filter cake is purified by a short-flow rectification system in a pressure of 6 Kpa and a temperature of 200° C. to obtain pure DMT. The purity of DMT obtained by the waste polyester recycling method provided in this embodiment is 99.5%, and the yield is 92%.

Embodiment 2

It is the same as the recycling method used in the embodiment 1, except that the raw material is waste polyester film, which is processed into fragments of (5 mm-10 mm)×(5 mm-10 mm) The purity of DMT is 99.5%, and the yield is 92.5%.

Comparative Embodiment 1

The raw material is waste polyester pellets made from granulation treatment. After testing, the intrinsic viscosity is 0.62 dl/g, the melting point is 260° C., the average particle size is <10 mm, and the moisture content is <0.5%. The waste polyester pellets are fed into the screw extruder 7 from the waste polyester tank 5 through the rotary feeder 6 and melted therein, and then filtered through the filter 8 to remove un-melted impurities. Thereafter the melted material is continuously sent to the alcoholysis tank 21. The melting temperature of the screw extruder 7 is 275° C., and the filtration accuracy, i.e. pore size, of the filter 8 is 150 μm. The difference from embodiment 1 is that the waste polyester pellets are not added with the alcoholysis agent, ethylene glycol, during the melting process of the screw extruder 7. After testing, the viscosity of the melt was 0.60 dl/g, the melting point was 255° C., and the switching cycle of the filter 8 is 15 days.

The other steps are the same as in embodiment 1. In the actual production process, it is found that the current of the motor 22 in the alcoholysis tank often rises abnormally. After sample analysis of the alcoholysis product, the content of BHET monomers in alcoholysis product is 63% and the total content of monomers, dimers, trimers and tetramers is 83%. The final recycled DMT has a purity of 99.5% and a yield of 86%.

Comparative Embodiment 2

The raw material is waste polyester pellets made from granulation treatment. After testing, the intrinsic viscosity is 0.62 dl/g, the melting point is 260° C., the average particle size is <10 mm, and the moisture content is <0.5%. The waste polyester pellets are fed into the screw extruder 7 from the waste polyester tank 5 through the rotary feeder 6 and melted therein, and then filtered through the filter 8 to remove un-melted impurities. Thereafter the melted material is continuously sent to the alcoholysis tank 21. The melting temperature of the screw extruder 7 is 275° C., and the filtration accuracy, i.e. pore size, of the filter 8 is 150 μm. The difference from embodiment 1 is that the waste polyester pellets are not added with the alcoholysis agent, ethylene glycol, during the melting process of the screw extruder 7. After testing, the viscosity of the melt was 0.60 dl/g, the melting point was 255° C., and the switching cycle of the filter 8 is 15 days.

The other steps are the same as in embodiment 1. The temperature of the alcoholysis reaction is 190° C., and the material residence time, i.e. the alcoholysis time, is 90 minutes. After sample analysis of the alcoholysis product, the content of BHET monomers in alcoholysis product is 75% and the total content of monomers, dimers, trimers and tetramers is 94%. The final recycled DMT has a purity of 99.5% and a yield of 92%.

Comparative Embodiment 3

Please refer to the comparative embodiment 2. The difference is that the temperature of the alcoholysis reaction is 220° C., and the material residence time, i.e. the alcoholysis time, is 60 minutes.

The content of BHET monomers in alcoholysis product is 74% and the total content of monomers, dimers, trimers and tetramers is 93%. The final recycled DMT has a purity of 98.2% and a yield of 88%.

The test method of intrinsic viscosity is in accordance with the provisions of GB/T 14190-2017, i.e. Intrinsic Viscosity Measurement Method A (capillary viscometer method, solvent mass ratio is 60:40).

In other embodiments, the alcoholysis process can also be distributed in two or more alcoholysis tanks connected in series.

For example, after alcoholysis from the first alcoholysis tank, the melt is continuously fed to the second alcoholysis tank connected in series to continue alcoholysis. As a result, the alcoholysis reaction is more thorough, the degree of alcoholysis is more consistent, the yield of alcoholysis monomers is improved, and the efficiency of the subsequent transesterification reaction and product purity are improved.

Although the above embodiments have been described, those skilled in the art can make other changes and modifications to these embodiments once they have learned the basic inventive concept. Therefore, the above descriptions are only the embodiments of the present invention, and thus does not limit the patent protective scope of the present invention. Similarly, any equivalent structure or equivalent process transformation made by using the present specification and the drawings, or directly or indirectly applied to other relevant technical fields, shall be included in the patent protective scope of the present invention.

We claim:
1. A method for recycling waste polyester comprising:
material pretreatment: dewatering and deoxidizing waste polyester material to obtain waste polyester as raw material;
feeding in melted state: after the step of material pretreatment melting the waste polyester to obtain melted waste polyester and feeding the melted waste polyester to a alcoholysis tank, wherein before the step of feeding the melted waste polyester to the alcoholysis tank the alcoholysis agent is added in the melted waste polyester for preliminary alcoholysis and the alcoholysis agent is ethylene glycol;
alcoholysis: the melted waste polyester, an alcoholysis agent, and an alcoholysis catalyst undergo depolymerization reaction in the alcoholysis tank to obtain alcoholysis product; and
transesterification: the transesterification agent, a transesterification catalyst and the alcoholysis product undergo transesterification reaction in the transesterification tank;
wherein based on the weight of the waste polyester raw material, the dosage of the alcoholysis agent is 10 ppm-5% during the preliminary alcoholysis.
2. The method for recycling waste polyester according to claim 1, wherein in the step of alcoholysis, the weight ratio of the melted waste polyester, the alcoholysis agent, and the alcoholysis catalyst is 1:1.0-2.0:0.003-0.03.

3. The method for recycling waste polyester according to claim 2, wherein the alcoholysis catalyst is potassium carbonate or zinc acetate and is prepared into an ethylene glycol solution with a mass concentration of 10%-70% and added into the alcoholysis tank.

4. The method for recycling waste polyester according to claim 1, wherein the transesterification agent is methanol, and the weight ratio of the melted waste polyester to the transesterification agent is 1:1 to 3.0.

5. The method for recycling waste polyester according to claim 1, wherein the transesterification catalyst is sodium hydroxide or potassium carbonate, and the weight ratio of the melted waste polyester to the transesterification catalyst is 1:0.002-0.05.

6. The method for recycling waste polyester according to claim 5, wherein the weight ratio of the melted waste polyester to the transesterification catalyst is 1:0.003-0.02.

7. The method for recycling waste polyester according to claim 5, wherein the transesterification catalyst is prepared into an ethylene glycol solution with a mass concentration of 10%-70% and added to the transesterification tank.

8. The method for recycling waste polyester according to claim 1, wherein the reaction temperature is 180° C.-200° C. and the reaction time is 60 min-120 min in the step of alcoholysis.

9. The method for recycling waste polyester according to claim 1, wherein the reaction temperature is 60° C.-80° C. and the reaction time is 30 min-90 min in the step of transesterification.

10. The method for recycling waste polyester according to claim 1, wherein the waste polyester is made of uniform waste polyester pellets, and the waste polyester pellets are fed into a screw extruder from a waste polyester tank through a rotary feeder for melting to form a melted material, and the conveying amount of the melted material is adjusted by the rotational speed of the screw extruder, and the rotary speed is controlled based on a liquid level of the alcoholysis tank.

11. The method for recycling waste polyester according to claim 10, wherein the melted material is filtered through a filter to remove un-melted impurities before conveying to the alcoholysis tank.

* * * * *